United States Patent [19]
Finlayson

[11] Patent Number: 4,764,944
[45] Date of Patent: Aug. 16, 1988

[54] METHODS FOR POSITIONING AN INTERNAL PORTION OF A BODY RELATIVE TO AN EXTRACORPOREAL REFERENT

[75] Inventor: Birdwell Finlayson, Gainesville, Fla.

[73] Assignee: University of Florida, Gainesville, Fla.

[21] Appl. No.: 875,474

[22] Filed: Jun. 18, 1986

[51] Int. Cl.$^4$ .............................................. A61B 6/08
[52] U.S. Cl. ..................................... 378/20; 378/205; 29/407
[58] Field of Search ............................ 378/20, 34, 205; 29/407

[56] References Cited

U.S. PATENT DOCUMENTS

| | | | |
|---|---|---|---|
| 4,118,631 | 10/1978 | Froggatt | 378/205 |
| 4,297,582 | 10/1981 | Schweirz et al. | 378/20 |
| 4,455,667 | 6/1984 | Schweirz et al. | 378/20 |
| 4,573,179 | 2/1986 | Rutt | 378/20 |
| 4,583,242 | 4/1986 | Vinegar et al. | 378/20 |
| 4,633,494 | 12/1986 | Klausz | 378/205 |

FOREIGN PATENT DOCUMENTS

3436444  4/1986  Fed. Rep. of Germany ........ 378/20

*Primary Examiner*—Timothy V. Eley
*Attorney, Agent, or Firm*—Cooper & Dunham

[57] ABSTRACT

Procedure for positioning a small internal portion of a body at a predetermined point relative to an external source of shock waves or the like, for treatment of the positioned body portion, wherein a volume of the body including the body portion is imaged with penetrating radiation by each of two detectors respectively aligned with viewing axes intersecting at the predetermined point; the coordinates of the body portion on each of the two images thus produced are measured and corrected for imaging distortions; from these corrected coordinates, there is derived a set of three-dimensional spatial coordinates for the body portion, defining a displacement vector giving the magnitude and direction of body motion required to position the body portion at the predetermined point; and the body is displaced with a resultant motion of that magnitude and direction.

9 Claims, 5 Drawing Sheets

METHODS FOR POSITIONING AN INTERNAL PORTION OF A BODY RELATIVE TO AN EXTRACORPOREAL REFERENT

BACKGROUND OF THE INVENTION

This invention relates to methods for positioning a small internal portion of a body at a predetermined point relative to an extracorporeal referent. In an important aspect, the invention is concerned with positioning a small internal body portion detectable by penetrating radiation, such as a concretion within the body of a living human patient, at a predetermined point relative to an external energy source or the like, e.g. for treatment of the body portion with focused or directional wave energy from the source.

One specific application of the invention, which will be particularly considered herein for purposes of illustration, is in the treatment of kidney stones by extracorporeal shock wave lithotripsy (ESWL). Apparatus and procedures for ESWL treatments are described, for example, in U.S. Pat. No. 3,942,531, No. 4,530,358, and No. 4,539,989, and in Ch. Chaussy et al., *Extracorporeal Shock Wave Lithotripsy* (Basel: Karger, 1982), the disclosures of all of which are herein incorporated by this reference.

Typical ESWL apparatus includes a water-filled shock wave focusing chamber in the form of a partial ellipsoid, truncated orthogonally to the major axis, mounted on (and opening into) a patient-receiving water tank, and so arranged that the first focus of the ellipsoid is within the focusing chamber while the second focus of the ellipsoid is outside the focusing chamber but within the tank. Means such as an arc discharge device are provided for generating high energy shock waves at the first focus of the ellipsoid. The patient to be treated is suspended in the tank on a cradle movably carried by a gantry. With the patient so positioned that the kidney stone to be treated is located at the second focus of the ellipsoid, reflected shock waves generated in the focusing chamber (and propagating through the chamber and tank water and the patient's body) cause the stone to disintegrate. Thereby, in at least many instances, the patient is ultimately able to pass the stone fragments without surgical intervention.

Precise positioning of the stone at the ellipsoid second focus within the tank is critically important, both to achieve the desired result of stone disintegration by the shock waves and also to minimize the possibility of detrimental effects of the shock waves on other portions of the patient's body. To this end, in current practice, two X-ray image intensifiers (herein sometimes also termed fluoroscopes) are mounted above the tank, pointing downwardly toward the patient position, and are oriented at an angle to each other such that their respective viewing axes converge and intersect at the second focus of the ellipsoid. Each fluoroscope is movable along its viewing axis. The two viewing axes define a plane, oblique to the horizontal, which intersects the patient's body transversely. Two X-ray sources (X-ray tubes) are disposed below the tank, in positions for respectively directing radiation upwardly through the patient to the two fluoroscopes along the aforementioned viewing axes. The outputs of the fluoroscopes are respectively displayed on monitors each having a cathode ray tube provided with crosshairs representing rectangular-coordinate axes perpendicular to (and intersecting at) the associated fluoroscope viewing axis.

Thus, an operator viewing these monitors can ascertain the positional relation of a kidney stone (which is imaged by X-radiation distinguishably from surrounding body tissue) to the viewing axes of the two fluoroscopes. Owing to the above-described orientation of the fluoroscopes, the kidney stone is properly positioned at the ellipsoid second focus when, but only when, its image is centered in the crosshairs of both monitors.

Heretofore, patient positioning in ESWL apparatus of the described type has been an essentially manual procedure, in which the operator, observing the monitor screens (after the patient has been lowered into the tank on the gantry cradle), manipulates the gantry controls to move the gantry and patient until the kidney stone image is centered on both monitors. This procedure can be relatively difficult and time-consuming; in particular, it involves undesirably long exposure of the patient to X-radiation, since the kidney stone image must be continuously viewed on the monitors as the patient is moved. Moreover, in some circumstances, the gantry cradle may drag across and damage the focusing chamber while the operator is moving the gantry in accordance with visual observation of the monitor.

SUMMARY OF THE INVENTION

The present invention contemplates the provision of a new and improved method of positioning a small internal portion of a body at a predetermined point relative to an extracorporeal referent, the body portion being detectable by penetrating radiation and the body being initially so disposed that the body portion is generally adjacent the predetermined point. Stated broadly, the method of the invention comprises the steps of viewing the body with penetrating radiation along two convergent viewing axes intersecting at the predetermined point for producing two images of the interior of the body as viewed by the penetrating radiation respectively along the two viewing axes, each of the images including a portion representing the aforesaid body portion; determining, from the two images, two-dimensional coordinates of the projections of the imaged body portion by the penetrating radiation on two notional planes respectively perpendicular to the viewing axes of the images, thereby to establish two sets of two-dimensional body portion coordinates, one for each image; from the two sets of two-dimensional coordinates, deriving for each image spatial coordinates of the imaged body portion in a coordinate system having as one axis the viewing axis of the image, thereby to establish two sets of three-dimensional body porton coordinates, one for each image; transforming these two sets of three-dimensional coordinates into a single set of three-dimensional coordinates in a common coordinate system in which the coordinates of the predetermined point are known, this single set of three-dimensional coordinates representing the location of the body portion in the last-mentioned system, thereby to determine the magnitude and direction of movement of the body required to position the body portion at the predetermined point; and displacing the body with a resultant motion having that magnitude and direction.

In exemplary and currently preferred embodiments of the invention, the viewing step is performed by directing penetrating radiation, from two sources of radiation disposed below the body, respectively along each of the two viewing axes through the body; receiving penetrating radiation from the sources, after passage of the radiation through the body, with two radiation detectors disposed above the body and respectively aligned with the two viewing axes, each of the detectors producing an output convertible into a two-dimensional image of the body volume through which radiation received by that detector has passed, in an image plane perpendicular to the viewing axis with which the detector is aligned; and converting the output of each detector into such two-dimensional image. It will be appreciated, of course, that "above" and "below" are used herein only as relative terms, since the absolute orientation of the sources and detectors is immaterial to the invention as long as the sources and the detectors are opposed with respect to the body. By way of specific example, the radiation sources may be X-ray tubes, and the detectors may be image intensifiers (fluoroscopes) having outputs imaged on cathode ray tubes, as in known ESWL apparatus of the type described above.

A significant advantage of the present method for medical applications is that it enables the body to be positioned using information derived from two concurrently produced initial images, necessitating only relatively brief irradiation of the patient while the requisite coordinates are obtained, rather than (as in prior practice) involving continuing exposure of the patient to radiation during the actual positioning of the body by an operator watching images of the moving body. The reduction in radiation exposure thus afforded by the invention may exceed 50%. At the same time, since the magnitude and direction of body motion are determined in this method from initial image information rather than by continuing observation of the changing position of the moving body portion, it is essential that the initial position coordinates of the body portion relative to the predetermined point be determined with fairly high accuracy. Since the imaged body portion is typically off center (displaced from the viewing axis) in one or both images, and since the observed or apparent coordinates of off-center portions of such images differ from the true spatial coordinates of the imaged object or body portion owing to various factors, it is necessary to apply compensating modifications or corrections to the apparent coordinates in order to obtain useful approximations of the true spatial coordinates. Important particular features of the invention reside in the inclusion, in the method broadly set forth above, of steps or procedures for modifying the apparent image coordinates of the body portion to compensate for these factors, which include parallax magnification and (with cathode ray tube images) electronic magnification and so-called vignetting.

Compensation for vignetting and electronic magnification is accomplished in the step of determining the two-dimensional coordinates, by modifying the observed position of the body portion in each image in accordance with data obtained by calibration. Parallax magnification is dependent on the source-to-detector spacing, and in the case of detectors movable along their respective viewing axes (e.g., to accommodate bodies of different sizes, as in known ESWL apparatus), the correction for parallax magnification (accomplished in the step of deriving two sets of three-dimensional coordinates) involves determining the location of each detector along its viewing axis when each image is produced.

Stated in terms of rectangular coordinate viewing systems, for each image there is posited a fluoroscope coordinate system in which the x axis is the viewing axis along which the image is taken. The displayed image is a projection in the aforementioned notional plane, viz. the plane perpendicular to the viewing axis at the input face of the detector which produces the image. Thus, only the apparent y and z coordinates of the body portion are directly measurable on the displayed image. The viewing axes of the two images, intersecting at the predetermined point, define a plane (herein termed the viewing plane) which also contains the y axes of the two fluoroscope systems; and the z axes of the two fluoroscope coordinate systems coincide as a common perpendicular to the viewing plane. With this geometry, the x coordinates of the body portion in the two fluoroscope coordinate systems can be readily derived from the corrected y and z coordinates determined from the image data, as taken together with the measured positions of the fluoroscopes along the respective viewing axes and preestablished measurements of system geometry. Thus, for each image, there is established a three-dimensional set of coordinates for the body portion.

Transformation of these two sets of three-dimensional coordinates into a single set of body portion coordinates can be accomplished, in accordance with the invention, by rotating the two major coordinate systems about their common z axis, until their y axes coincide in the viewing plane, their x axes then also coinciding in the same plane in a line bisecting the angle formed between the two viewing axes. The origin of this single or combined coordinate system is still the predetermined point to which the body portion is to be moved. Conveniently, a further rotation may be effected to conform to the machine coordinates of the apparatus in which the body portion is to be positioned. For instance, in an illustrative ESWL apparatus, the viewing plane is oblique to the horizontal, while the machine coordinate system to which the patient-carrying gantry is referred has a vertical z axis and horizontal x and y axes; the x axis of the aforementioned combined coordinate system in the viewing plane lies in the xz plane of the machine coordinate system, and the y axis of the combined viewing plane coordinate system coincides with the y axis of the machine coordinate system, so that rotation of the combined viewing plane coordinate system about its y axis brings the latter system into coincidence with the machine coordinate system.

Frequently, the two three-dimensional sets of body portion coordinates respectively derived from the two images do not precisely coincide when they are transformed into a common coordinate system, e.g. as a result of imprecise measurement and/or compensation for distorting factors. That is to say, the spatial locations respectively identified by these two sets of coordinates may be somewhat spaced apart in the common coordinate system. When this occurs, it is necessary first to determine whether the two locations thus identified both in fact represent the same object, viz. the body portion to be positioned. In accordance with the invention, the distance between the two locations is compared with a predetermined value; if that distance is less than or equal to the predetermined value, then the coordinates of the midpoint between the two locations are derived from the coordinates of the two locations, and that midpoint is taken as the situs of the body portion.

Once the coordinates of the body portion in the final single coordinate system have been established (either by coincidence of the two sets of coordinates respectively derived from the two images, or by calculation of midpoint coordinates as just described), these coordinates and the coordinates of the predetermined point define a displacement vector representing the magnitude and direction of motion of the body needed to bring the body portion to the predetermined point. With this information, the body can be moved either linearly or (as a further advantage of the invention, if direct linear displacement would cause interfering contact with and possible damage to adjacent apparatus elements) by a roundabout path, in either case with a resultant motion having the magnitude and direction represented by the displacement vector.

The invention may be further understood by reference to exemplary apparatus for use in the practice of the foregoing method in a system for treating a small internal portion of a body with shock waves or the like from an external energy source, wherein the body portion is to be positioned at a predetermined point relative to the energy source, the system including means for moving the body and two detectors (for receiving penetrating radiation after passage through the body) having viewing axes intersecting at the predetermined point, each detector being movable along its viewing axis and each producing a cathode ray tube image. Such apparatus includes, in combination, means including a stylus for sensing the position of an operator-selected image portion on a cathode ray tube screen and producing a first output signal representing the position on the screen of the selected image portion; means respectively associated with the two detectors for sensing the positions of the detectors along their viewing axes and producing second and third output signals respectively representing those positions; and means for combining the first, second and third output signals to produce an information output representing the magnitude and direction of body displacement needed to bring the body portion to the predetermined point.

Further features and advantages of the invention will be apparent from the detailed description hereinbelow set forth, together with the accompanying drawings.

DETAILED DESCRIPTION

The invention will be described with reference to its use in ESWL apparatus of known type, having features generally set forth in one or more of the above-cited patents and/or in the above-cited Chaussy et al. publication. An example of such apparatus, arranged for treatment of a kidney stone in a living human patient P, is illustrated schematically at 10 in FIGS. 1 and 2. As there shown, such apparatus includes a water tank 11, adapted to be filled with water 12 and dimensioned to receive an adult patient P in a generally recumbent position. The patient is supported on a cradle 14 carried by an overhead gantry 16, which is adapted to impart to the cradle (and thus to the patient) all modes of motion, viz. lateral, longitudinal, and vertical, necessary to position the patient precisely at a desired location within the tank for treatment. Once positioned, the patient is held securely and stably in the selected location by the cradle and gantry. Means (not shown) such as a motor are provided for moving the gantry in response to manipulation of a control system (also not shown) by an operator; the gantry position at any given time, with reference to the machine coordinate system described below, is sensed and displayed by an instrumentality 18 (XYZ display).

Figure 1:
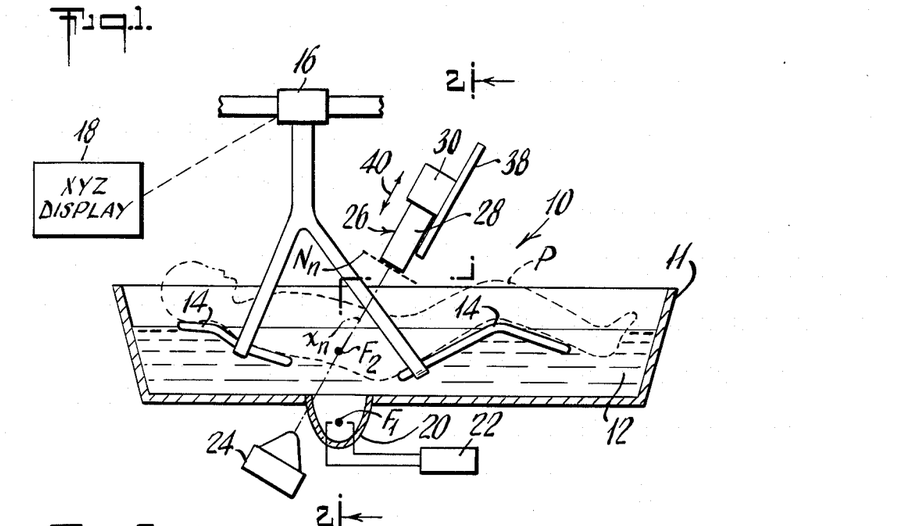
FIG. 1 is highly simplified schematic sectional side elevational view of an example of ESWL apparatus with which the method of the present invention may be practiced.

A hollow truncated ellipsoidal shock wave focusing chamber 20 is mounted in the floor of the tank 11 so as to open upwardly at an angle of about 14.28° from the vertical into the interior of the tank; i.e., although for convenience of illustration the chamber is shown in FIG. 1 as if its axis (containing points $F_1$ and $F_2$) were vertical, in fact the latter axis in the view of FIG. 1 should be at 14.28° to the vertical. This chamber 20 defines part of the surface of an ellipsoid of revolution having a first focus $F_1$ within the chamber and a second focus $F_2$ above the chamber but within the tank. The ellipsoid is configured to locate $F_2$ sufficiently above the tank floor so that an internal portion of a patient's body can be positioned to coincide with $F_2$. Associated with the chamber 20 is an arc discharge device 22 having a spark gap positioned at focus $F_1$ within the chamber. In operation, with the interior of the chamber 20 and the tank 11 filled with water, a spark discharge at the gap generates a high energy shock wave in the water at $F_1$. Direct and reflected components of this shock wave propagate upwardly through the tank, with a focus or intensity maximum at $F_2$. If a human patient having a concretion such as a kidney stone within his or her body is suspended in the tank water by the cradle and gantry, with the kidney stone positioned at $F_2$ and the surrounding region of the body immersed in the tank water, a succession of such spark-generated shock waves will cause the kidney stone to disintegrate without damaging other body portions. For safe and effective treatment, however, careful positioning of the kidney stone at $F_2$ is highly important; and since the kidney stone is a small internal portion of the body, it is located and positioned with the aid of X-ray (fluoroscopic) examination of the patient after the patient's body has been initially so disposed that the kidney stone-containing region of the body is generally adjacent $F_2$.

More particularly, the ESWL apparatus is provided with a pair of X-ray sources (X-ray tubes) 24, 25 disposed beneath the tank 11 so as to direct X radiation upwardly through the tank along oblique paths respectively having axes $x_n$ and $x_s$ intersecting at $F_2$. A pair of detectors or fluoroscopes 26, 27 are mounted above the tank, respectively in alignment with the axes $x_n$ and $x_s$, which are hereinafter referred to as viewing axes. Each fluoroscope is adapted to receive X radiation from its associated X-ray source after the radiation has passed through the tank and patient P, and to produce an output that is convertible into a two-dimensional cathode ray tube (CRT) image of the body volume traversed by the radiation received by the fluorosocope. In the form shown, each fluoroscope comprises an image intensifier 28 or 29 and a television camera 30 or 31 which transmits the fluoroscope output for display on the screen 32 or 33 of the cathode ray tube of an associated television monitor 34 or 35. Thus, two images are displayed, one for each fluoroscope, on the screens of the two monitors respectively connected to the two fluoroscopes.

Each of the fluoroscopes 26 and 27 is mounted (by means shown as a track 38 in FIG. 1) for movement in the directions indicated by arrow 40 in FIG. 1, viz. along the viewing axis $x_n$ or $x_s$ with which it is aligned, being provided with a worm gear drive (not shown) to effect such movement. This axially directed movement, through a restricted range of positions, permits the fluoroscopes to be brought close to the patient's body while accommodating patients of differing girth and/or permitting unobstructed movement of the patient's body into the proper position. The fluoroscopes are also pivotally movable out of the space above the tank to facilitate introduction of a patient to the tank.

Figure 2:
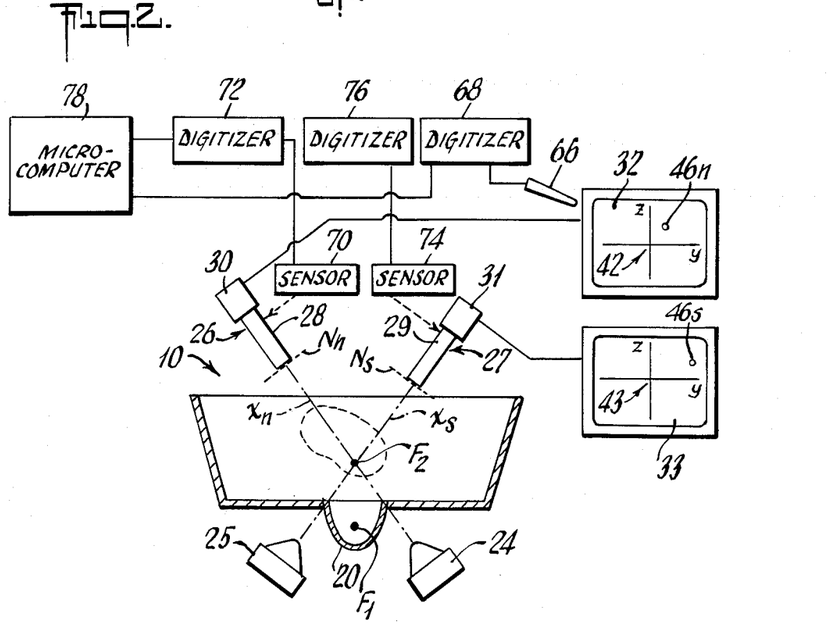
FIG. 2 is a view taken along the line 2—2 of FIG. 1, also showing diagrammatically a particular example of apparatus for practice of the invention, as incorporated in the ESWL apparatus of FIG. 1.

The CRT screen 32 of monitor 34 (connected to fluoroscope 26) is shown as provided with a referent 42 comprising cross-hairs representing rectangular coordinate axes $y_n$ and $z_{n,s}$ which are perpendicular to each other and to the viewing axis $x_n$ of the fluoroscope 26. Similarly, the CRT screen 33 of monitor 35 (connected to fluoroscope 27) is provided with a referent 43 comprising cross-hairs representing rectangular coordinate axes $y_s$ and $z_{n,s}$ which are perpendicular to each other and to the viewing axis $x_s$ of the fluoroscope 27. Thus, the body image produced on each screen is a two-dimensional projection in a plane perpendicular to the viewing axis of the associated fluoroscope, the viewing axis being centered on the screen at the intersection of the cross-hairs. A concretion such as a kidney stone included in the imaged body region is discernible in each image as a spot (46n or 46s) visually distinguishable from surrounding body tissue, because the concretion is less transmissive to X radiation than is the surrounding tissue. Since the two fluoroscope viewing axes $x_n$ and $x_s$ converge and intersect at $F_2$, a kidney stone is properly positioned at $F_2$ if but only if the spots 46n and 46s representing it on the two CRT images are both centered on the cross hairs of the respective CRT screens. If either or both kidney stone image spots are away from the cross-hair intersections, the kidney stone is not yet located at $F_2$ and the body must be moved before shock wave treatment can begin.

The apparatus as thus far described is, as already indicated, generally known or conventional for ESWL treatment. In currently used positioning procedures in such apparatus, the operator initially positions the patient in the tank so that the kidney stone location within the patient's body is generally adjacent the location of $F_2$; then, while continuously or repetitively irradiating the patient from both X-ray sources and observing the location of spots 46n and 46s on the two monitor screens, the operator manipulates the gantry controls to move the patient until the spots 46n and 46s both coincide with the cross-hair intersections on the respective screens. The present invention, now to be described, enables the initial position of a kidney stone relative to $F_2$ to be derived from two single initial static images (respectively displayed on the two monitor screens), with accuracy sufficient to determine the resultant direction and magnitude of body displacement that will bring the stone to $F_2$. This direction and magnitude of motion may then be imparted to the body, either directly or circuitously (e.g., when necessary to avoid possibly damaging contact of the cradle with the focusing chamber), by operation of the gantry controls without further or continuing irradiation of the patient.

Figure 3:
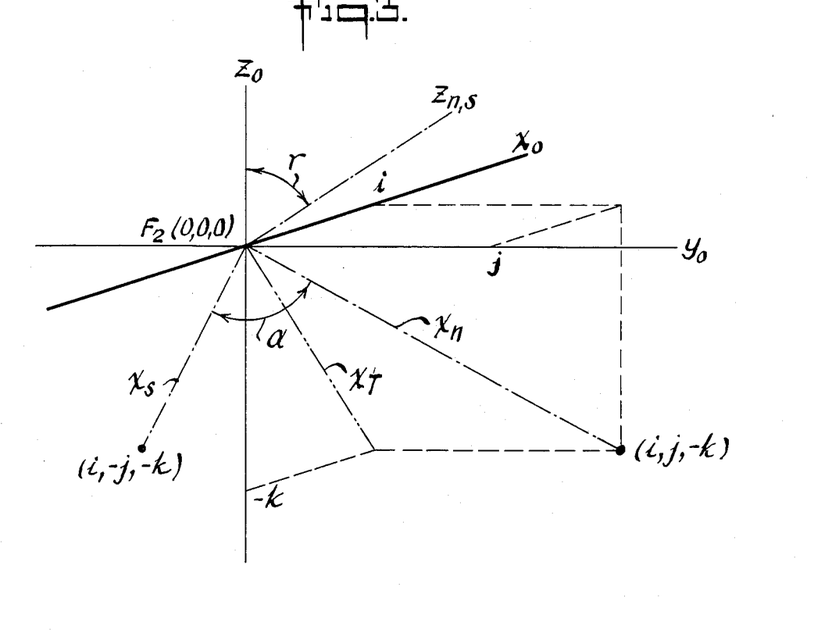
FIG. 3 is a diagram showing a three-dimensional rectangular coordinate system ($x_o$, $y_o$, $Z_o$) for the apparatus of FIG. 1 and representing features of apparatus geometry pertinent to the practice of the present method in an illustrative embodiment.
Figure 4:
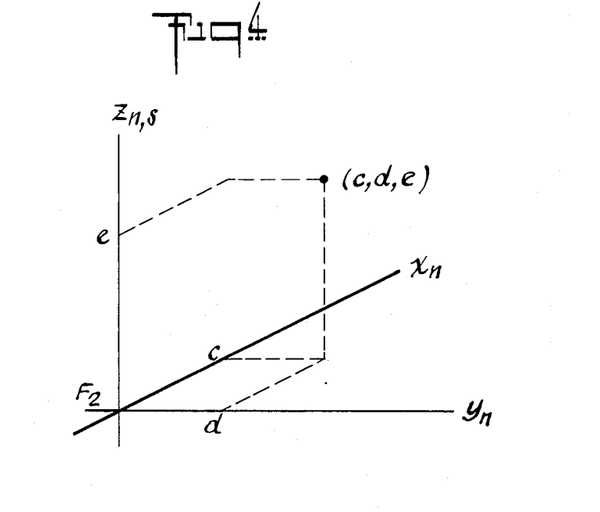
FIG. 4 is a diagram showing the position of an exemplary point (c, d, e) relative to a three-dimensional rectangular coordinate system for one fluoroscope of the apparatus of FIG. 1.

Features of the geometry of the above-described ESWL apparatus 10 pertinent to an understanding of the present invention are illustrated in FIGS. 3 and 4. In FIG. 3, the machine coordinate system of the ESWL apparatus 10 is the three-dimensional rectangular coordinate system having horizontal axes $x_o$ and $y_o$ and vertical axis $z_o$ with an origin at $F_2$, the $x_o$ axis being oriented lengthwise of the patient position in the tank 11. The positions of the two fluoroscope viewing axes $x_n$ and $x_s$ in the machine coordinate system are defined by the origin $F_2$ (at which the two viewing axes intersect) and, respectively, by the coordinates i, j, $-k$, and i, $-j$, $-k$; thus the two viewing axes diverge symmetrically (at equal but opposite angles) from the $x_o$-$z_o$ plane. The viewing plane, viz. the plane in which viewing axes $x_n$ and $x_s$ both lie, is oblique to the horizontal ($x_o$-$y_o$ plane) and is oriented to intersect a patient transversely. In the viewing plane, the angle a between axes $x_n$ and $x_s$ is bisected by the $x_o$-$z_o$ plane, which intersects the viewing plane at line $x_T$. This line $x_T$, then, lies both in the $x_o$-$z_o$ plane and in the viewing plane, and also passes through $F_2$, forming equal but opposite angles a/2 with the two viewing axes.

For each of the two fluoroscopes 26 and 27, there is defined a three-dimensional rectangular coordinate system for which the fluoroscope viewing axis $x_n$ or $x_s$ is the x axis. The origins of both fluoroscope coordinate systems are at $F_2$, and they share a common z axis (designated $z_{n,s}$) lying in the $x_o$-$z_o$ plane. Consequently, the y axis of each fluoroscope coordinate system (designated $y_n$ for fluoroscope 26, and $y_s$ for fluoroscope 27) lies in the viewing plane. The coordinate system of fluoroscope 26 is represented in FIG. 4, which illustrates the spatial coordinates c, d, e of an object (e.g., a kidney stone) in that system.

It will be seen that the $y_n$ and $z_{n,s}$ axes define a plane containing $F_2$ and perpendicular to the viewing axis $x_n$ of the fluoroscope 26. The image plane of the monitor screen 32 (FIG. 2) may be considered to be parallel to this plane, with referent 42 representing the $y_n$ and $z_{n,s}$ axes therein. In the absence of imaging distortions, a kidney stone image spot (46n) on screen 42 would represent a geometric projection of the imaged kidney stone on the $y_n$-$z_{n,s}$ plane, and the y and z spatial coordinates (d and e, in FIG. 4) of the kidney stone in the fluoroscope 26 coordinate system would be the same as the measured coordinates of spot 46n relative to referent 42. Similarly, the $y_s$ and $z_{n,s}$ axes define a plane containing $F_2$ and perpendicular to the viewing axis $x_s$ of fluoroscope 27; the image plane of monitor screen 33 may be considered to be parallel to the latter plane, with referent 43 representing axes $y_s$ and $z_{n,s}$, and the measured coordinates of an image spot 46s on screen 33 relative to referent 43 would equal the spatial y and z coordinates of the imaged kidney stone in the fluoroscope 27 coordinate system, except for imaging distortions. As hereinafter further explained, however, the measured positions of spots 46n and 46s relative to the respective referents 42 and 43 differ significantly (because of imaging distortions) from the spatial y, z coordinates of the object they represent in the respective fluoroscope coordinate systems.

Figures 5, 6, 7:
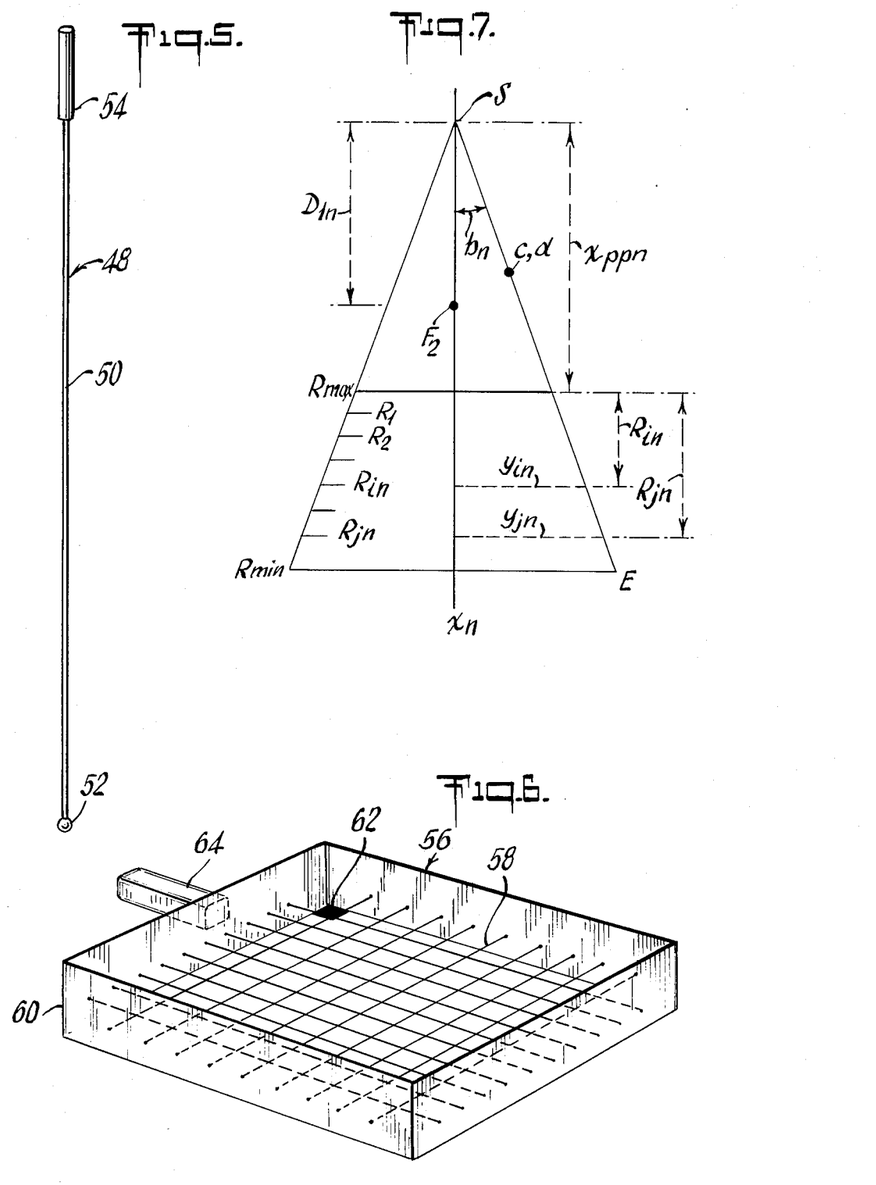
FIG. 5 is an elevational view of a calibrating instrument or eisenkugel employed in a calibrating procedure in the practice of the present method.
FIG. 6 is a perspective view of a calibrating grid structure employed in a calibrating procedure in the practice of the present method.
FIG. 7 is a diagram in explanation of the parallax correction included in the aforementioned embodiment of the method of the invention.

For the practice of the method of the invention in the present embodiment, it is necessary to pre-establish certain fixed dimensions of system geometry, viz. the angle a between the viewing axes $x_n$ and $x_s$ and the angle between the $x_n$-$x_s$ viewing plane and the horizontal $x_o$-$y_o$ plane of the machine coordinate system. These dimensions may be established by preliminary calibration operations, e.g. utilizing an eisenkugel 48 (FIG. 5). The eisenkugel is a steel rod 50, e.g. 2 mm. in diameter and one meter long, having a steel ball 52 (e.g. 4 mm. in diameter) at one end and a cylindrical enlargement 54 (e.g. about 7 mm. in diameter, and 5 cm. long) at the other end; the enlargement 54 friction fits into a hole (not shown) on the gantry 16, from which the rod 50 and ball 52 then depend vertically so as to enable the ball 54 to be positioned at $F_2$.

It is also necessary to establish calibration values for correcting imaging distortions. A calibrating grid structure 56 (FIG. 6) may be used for this purpose. The grid structure is formed by stringing fine-guage copper wires 58 through holes spaced 1 mm. apart in a square plastic case 60, and pulling the wire tight to define a grid pattern of 1 cm.×1 cm. squares. The grid is completely enclosed in the plastic case, which has a small square 62 marked in one corner for indicating the orientation of the grid when viewed through a fluoroscope, and a lateral handle 64 for attachment to a flexible manipulating arm (not shown).

An exemplary embodiment of apparatus with which the present method may be performed is illustrated diagrammatically in FIG. 2. This apparatus comprises, in combination with the gantry, X-ray sources, fluoroscopes, and CRT monitors already described, means including a stylus 66 and associated digitizer 68 for sensing the position of an operator-selected image portion (e.g., 46n or 46s) on either monitor screen and producing a first digital output signal representing the position on the screen of the selected image portion; means including a sensor 70 and associated digitizer 72 for sensing the position of the fluoroscope 26 along its viewing axis $x_n$ and producing a second digital output signal representing that position; means including a further sensor 74 and associated digitizer 76 for similarly sensing the position of fluoroscope 27 along its viewing axis $x_s$ and producing a third digital output signal representative thereof; and a programmable microcomputer 78 for receiving and combining the first, second, and third output signals to produce an information output (e.g. a digital readout) representing the magnitude and direction of body displacement needed to position a patient's kidney stone at $F_2$.

As will be understood, the arrangement of stylus 66 and digitizer 68 is such that when the operator positions the stylus at a selected portion of an image on screen 32 or 33, the digitizer 68 senses that position and produces a digital output (a set of screen coordinates) representative of the selected position on the screen relative to the referent 42 or 43. The sensors 70 and 74, with their respectively associated digitizers 72 and 76, may constitute sonic digitizers for directly measuring fluoroscope position. Alternatively, each of these sensors may include an arm on the worm gear drive of the associated fluoroscope, and a photoelectric cell and light source so disposed that the arm repetitively breaks the light path therebetween during operation of the worm gear drive, to produce a succession of pulses which are counted by the associated digitizer and converted to a digital signal representative of fluoroscope position on the viewing axis. The microcomputer is preferably arranged to perform both initial calibrations and the calculation, from the calibration data and the output signals of the three digitizers, of the location of the imaged kidney stone relative to $F_2$.

System calibration, for the practice of the present method, includes development of data or values for modifying the apparent coordinates of selected image spots on screens 32 and 33 to correct for three types of imaging distortion: electronic distortion, electronic magnification, and parallax magnification. Electronic distortion, introduced by projection of an image by a cathode ray onto a screen, is the so-called vignetting effect, viz. elongation of the image at the edges of the monitor screen as compared to the image scale at the center of the screen. Imposed on this radial distortion, there is also typically a side-to-side electronic distortion causing images to appear contracted at one edge of the screen as compared to the representation at the other edge. Calibration to correct for electronic distortion in fluoroscope 26 and screen 32 is performed by placing the grid structure 56 at $F_2$ in the $y_n$-$z_{n,s}$ plane of the coordinate system of fluoroscope 26, producing an X-ray image of the grid at $F_2$ on the screen 32 with the X-ray source 24 and fluoroscope 26, measuring the screen coordinates of the grid junctions on the image, and comparing these measured values with the ideal coordinates of a square grid pattern to develop an array of ratios describing the distribution of the distortion across the screen being calibrated. The procedure is then repeated for fluoroscope 27 and screen 33. If the vignetting parameters can be assumed to be angularly symmetrical, the distribution is fit to an exponential function of distortion ratio versus distance from screen center. If the vignetting parameters are not angularly symmetrical, then exponentially fit vignetting parameters having a minimum of eight equally spaced vectors based at screen center are fit with a Fourier function. In either case, the calibration data thus developed are stored for application to the apparent two-dimensional image coordinates represented by the output of digitizer 68, to correct those coordinates for electronic distortion. From the vignetting calibration, then, there is derived a set of values or function for each monitor screen for application to the directly measured screen coordinates $y_{32}$, $z_{32}$ or $y_{33}$, $z_{33}$ on screen 32 or 33 relative to the screen referent 42 or 43 to obtain first corrected values $y_{cor\,n}$, $z_{cor\,n}$ and $y_{cor\,s}$, $z_{cor\,s}$ of the coordinates; for example, the first corrected value $y_{cor\,n}$ of the y coordinate of spot 46n on screen 32 is a function of the measured screen coordinates $y_{32}$, $z_{32}$ and of the correcting value, which is itself a function of the position of the spot 46n on the screen.

The second type of distortion for which correction must be made is electronic magnification, which (for the system herein considered) is usually positive, i.e. causing any two points imaged on one of the screens 32 or 33 to be farther apart than the spatial points to which they correspond. Calibration for electronic magnification is performed by disposing the grid 56 against each fluoroscope face, substantially in a plane perpendicular to the fluoroscope viewing axis, viewing an X-ray image of the grid on the associated screen 32 or 33, and, after correcting the coordinates of the imaged grid junctions by application of the previously developed vignetting calibration data, measuring the spacing of the imaged grid junctions, and dividing this apparent grid spacing ($L_{cor\ n}$ or $L_{cor\ s}$) by the actual (1 cm) spacing ($L_{56}$) between junctions of the physical grid to determine for each screen a value of electronic magnification factor ($W_{32} = L_{cor\ n}/L_{56}$, $W_{33} = L_{cor\ s}/L_{56}$) to be applied to the sensed coordinates of an image spot 46n or 46s after correction for vignetting.

For any measured values $y_{32}$, $z_{32}$ of screen coordinates of a spot 46n on screen 32, then, one can obtain coordinates $y_{mn}$, $z_{mn}$ corrected for vignetting and electronic magnification, e.g. $y_{mn} = y_{cor\ n}/W_{32}$, while for any measured values $y_{33}$, $z_{33}$ of screen coordinates of a spot 46s on screen 33, one can similarly obtain corrected coordinates $y_{ms}$ and $z_{ms}$. These corrections, applied to any measured set of two-dimensional y,z screen coordinates, effectively eliminate electronic distortion (vignetting) and electronic magnification, so that the thus-corrected values $y_{mn}$, $z_{mn}$ or $y_{mx}$, $z_{ms}$ represent the coordinates of the projection of the object or body portion (represented by spot 46n or 46s) by penetrating radiation from sources 24 or 25 on a notional plane $N_n$ or $N_s$ perpendicular to the viewing axis $x_n$ or $x_s$ at the input face of the fluoroscope 26 or 27.

The y and z axes in either of the aforementioned notional planes are parallel to the axes $y_n$, $z_{n,s}$ or $y_s$, $z_{n,s}$ of the corresponding fluoroscope coordinate system, which latter axes lie in planes containing $F_2$ and respectively perpendicular to $x_n$ and $x_s$. The coordinates $y_{mn}$, $z_{mn}$ and $y_{ms}$, $z_{ms}$, nevertheless, do not represent the actual spatial y,z coordinates of the imaged object or body portion in either fluoroscope coordinate system, owing to parallax magnification. A further calibration procedure is employed to develop data needed to take into account the effect of parallax magnification and to enable determination of the spatial coordinates of the imaged body portion in each fluoroscope coordinate system.

The effect of parallax is a result of the divergence of X radiation emanating from the X-ray sources, which for present purposes may be treated as point sources. In FIG. 7, which is a diagram in the $x_n$-$y_n$ plane, the point of X-ray emanation from source 24 is indicated at S on the $x_n$ axis. SE represents a "ray" emanating from S and diverging from axis $x_n$ at the angle $b_n$. $R_{max}$ represents the maximum extension of the input face of fluoroscope 26 along axis $x_n$ toward S, $R_{min}$ represents the minimum extension of the same fluoroscope face, and $R_1$, $R_2$, ... $R_{in}$, ... $R_{jn}$ represent intermediate amounts of fluoroscope extension. Thus, the distance along $x_n$ between S and the notional plane at the input face of the fluoroscope, is in any instance equal to the sum of the fixed distance $x_{ppn}$ (from S to $R_{max}$) plus the value of R measured along $x_n$ from $R_{max}$ to the actual position of the fluoroscope face.

A point object or body portion having spatial coordinates x=c, y=d, z=e on the $x_n$, $y_n$, $z_{n,s}$ fluoroscope coordinate system and intercepted by divergent "ray" SE will have a radiation-projected y coordinate $y_{in}$ on the aforementioned notional plane at the input face of fluoroscope 26 if the fluoroscope input face is at $R_{in}$, and a y coordinate $y_{jn}$ on the notional plane if the fluoroscope input face is at $R_{jn}$ further away from S than $R_{in}$. This is the parallax magnification effect, which causes the corrected coordinates $y_{mn}$, $z_{mn}$ in the notional plane to differ from the actual spatial coordinates d,e. As shown, $y_j$ is greater than $y_i$, which is in turn greater than the spatial y coordinate (d) of the imaged body portion at c, d, e.

It will be apparent from FIG. 7 that the relation expressed by equation (1) below obtains, where $D_{1n}$ is the distance along $x_n$ from S to $F_2$, and the sign convention employed for the x axis is positive below $F_2$, negative above $F_2$ in FIG. 7, $F_2$ being the origin of the coordinate system to which c, d, and e refer. Further, since $R_{in}$ and $R_{jn}$ represent positions of the input face of the fluoroscope 26, it will be apparent that $y_{in}$ and $y_{jn}$ are respectively equal to $y_{mn}$ for the fluoroscope positions $R_{in}$ and $R_{jn}$. As will be understood, a like relation obtains for $z_{mn}$ (the z axis coordinate of the imaged body portion in the notional plane $N_n$ of fluoroscope 26, corrected for electronic distortion and electronic magnification); i.e., considering FIG. 7 as a diagram in the $x_n$-$z_{n,s}$ plane, and e as the z spatial coordinate of the imaged body portion in the fluoroscope 26 coordinate system, with $z_{in} = z_{mn}$ when the fluoroscope is at $R_{in}$, the relation expressed by equation (2) below obtains. Similar relations (equations (3) and (4) below) obtain for the corrected coordinates $y_{ms}$ and $z_{ms}$ in the coordinate system of fluoroscope 27, with $x_{pps}$ and $D_{1s}$ being the counterparts of $x_{ppn}$ and $D_{1n}$, and f, g, and h being respectively the spatial x, y and z coordinates of the imaged body portion, in that coordinate system. Determination of $x_{ppn}$, $D_{1n}$, $x_{pps}$ and $D_{1s}$ can therefore enable compensation for parallax effects in the derivation of three-dimensional coordinates for a body portion.

In ESWL apparatus of the type shown at 10 in FIG. 1, the X-ray sources are ordinarily fixed in relation to the focusing chamber, and the locations of $R_{max}$ and $R_{min}$ are likewise fixed relative thereto; hence $x_{ppn}$ and $D_{1n}$ are determinable constants. To ascertain their values in a precalibration procedure, the grid 56 is positioned at $F_2$, in the $y_n$-$z_{n,s}$ plane, and imaged with X radiation on screen 32, first with fluoroscope 26 at $R_{max}$ and then with fluoroscope 26 at $R_{min}$. For a grid junction for which the $y_n$ intercept is $L_{56}$ in the $y_n$-$z_{n,s}$ plane containing $F_2$, and the corrected y coordinates in the notional plane $N_n$ at $R_{max}$ and $R_{min}$ are respectively $L_{mn}(R_{max}) = L_{cor\ n}(R_{max})W_{32}$ and $L_{mn}(R_{min}) = L_{cor\ n}(R_{min})/W_{32}$, equation (5) below obtains.

$$\frac{y_{jn}}{x_{ppn} + R_{jn}} = \frac{y_{in}}{x_{ppn} + R_{in}} = \frac{d}{D_{ln} + c} = \tan b_n \quad (1)$$

$$\frac{z_{in}}{x_{ppn} + R_{in}} = \frac{e}{D_{ln} + c} \quad (2)$$

$$\frac{y_{ms}(is)}{x_{pps} + R_{is}} = \frac{g}{D_{ls} + c} \quad (3)$$

-continued $$\frac{z_{ms}(is)}{x_{pps} + R_{is}} = \frac{h}{D_{ls} + c} \quad (4)$$

$$\frac{L_{56}}{D_{ln}} = \frac{L_{mn}(R_{max})}{x_{ppn}} = \frac{L_{mn}(R_{min})}{x_{ppn} + R_{min}} \quad (5)$$

$R_{min}$ is measured by sensor 70, while $L_{56}$ is known and $L_{mn}(R_{max})$ and $L_{mn}(R_{min})$ are determinable by application of the electronic distortion and electronic magnification corrections to measured image values of $L_{32}$ (the apparent spacing between grid junctions on the image on screen 32 at $R_{max}$ and $R_{min}$); hence, from the relation just given, the values of $x_{ppn}$ and $D_{1n}$ can be calculated. The same calibration procedure is repeated to obtain the counterpart constants $D_{1s}$ and $x_{pps}$ for use with the image-derived data from fluoroscope 27.

Calibration is completed by measuring angle a (between $x_s$ and $x_n$) in the viewing plane and determining the angle between the viewing plane and the horizontal. For this purpose, the eisenkugel 48 is mounted on the gantry 16 as described above, and the gantry is moved by operation of its controls while the ball 52 is imaged with X radiation by both fluoroscopes until the ball images are centered on the crosshairs of both screens 32 and 33. At this point the coordinates shown on the XYZ display are read out. The gantry is moved again to selected other points, at each of which the coordinates shown on the XYZ display are again read out; for example, the gantry may be operated to move the ball 52 from $F_2$ to a point along viewing axis $x_n$, at which the ball image is centered on the crosshairs of screen 32 but has moved away from the crosshairs of screen 33, and thereafter the gantry may be moved again to position the ball at a point on axis $x_s$, at which the ball image is centered on the crosshairs of screen 33 but spaced from the crosshairs of screen 32. Since the coordinates shown on the XYZ display indicate gantry position relative to a coordinate system in which the xy plane is horizontal, the readout of the displayed coordinates for each of the three points just mentioned provides data sufficient to ascertain the magnitude of both of the angles to be measured.

The calibration data developed by the foregoing procedures are recorded or stored for use in the positioning method of the invention with the calibrated apparatus. Conveniently, these data are stored in the microcomputer 78, which is also (as already mentioned) conveniently programmed to process the raw incoming calibration information for deriving the calibration data therefrom, as well as to perform the calculations involved in the positioning method, using the calibration data and data measured in the steps of that method. Of course, all these operations may be performed in other ways as well, for example by hand.

Figure 10:
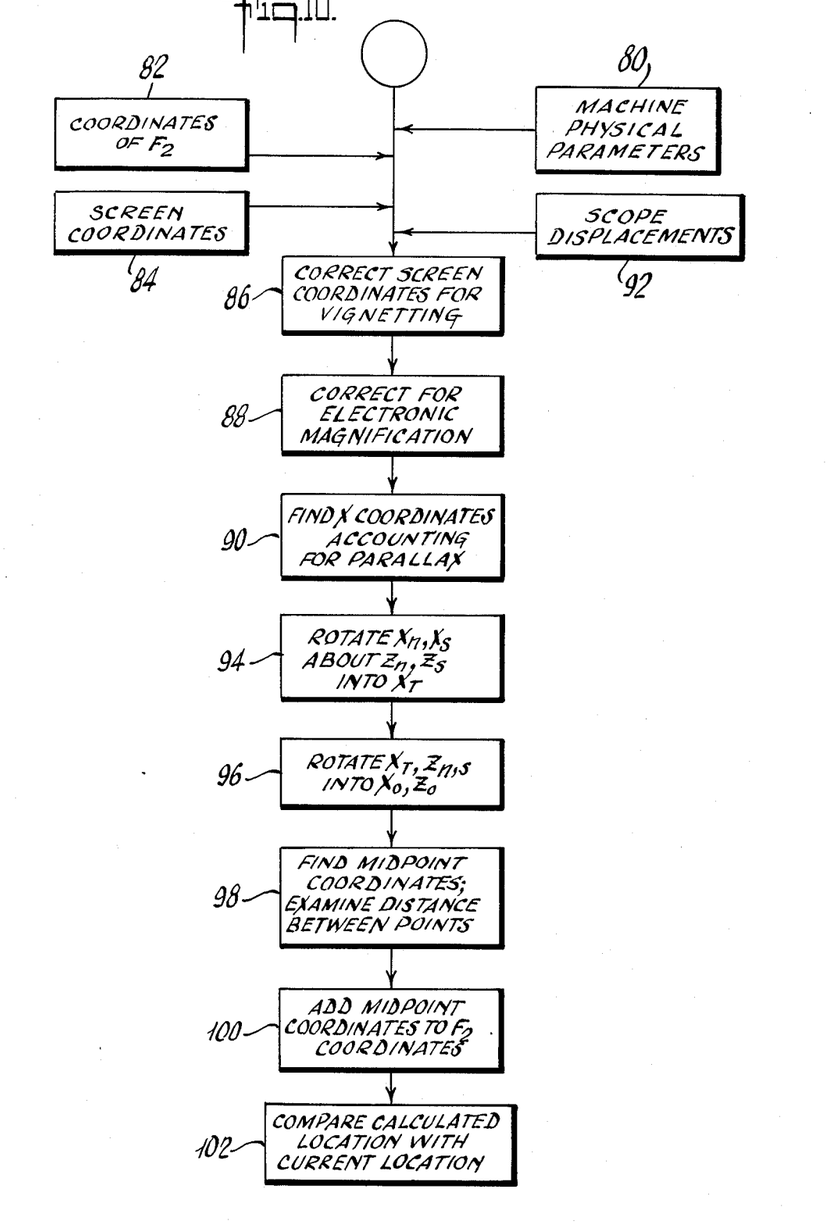
FIG. 10 is a flow chart representing various data acquisition and processing steps included in that embodiment of the method.

Sequential steps or operations in the practice of the present method to position a patient in the ESWL apparatus 10 are illustrated in flow chart form in FIG. 10. Once the calibration data have been established (boxes 80 and 82, FIG. 10), the patient P is placed on the cradle 14 and disposed (by operation of the gantry 16) within the water-filled tank 11, at a location at which the kidney stone to be treated is generally adjacent $F_2$. The fluoroscopes 26 and 27, which have been swung out of the way to admit the patient to the tank, are pivoted back into alignment with the respective viewing axes $x_n$ and $x_s$, and moved along these axes to positions close to the patient's body. The operator then energizes the X-ray sources 24 and 25 to produce, on screens 32 and 33, images of the region of the patient's body adjacent $F_2$.

Examining the displayed images on the two screens, the operator identifies on each screen a spot (46n or 46s) that appears to be an image of the kidney stone. The operator measures the screen coordinates $y_{32}$, $z_{32}$ (relative to referent 42) of the spot 46n on screen 32, and similarly measures the screen coordinates $y_{33}$, $z_{33}$ (relative to referent 43) of the spot 46s on screen 33 (box 84, FIG. 10). With the apparatus of FIG. 2, such measurement is accomplished by first placing the stylus 66 at the location on screen 32 of the selected spot 46n, and then placing the stylus at the location on screen 33 of the selected spot 46s. The digitizer 66, sensing the stylus position on each screen, responds to each sensed stylus position by supplying to microcomputer 78 digital signals representing the measured screen coordinates thereof.

The measured screen coordinates $y_{32}$, $z_{32}$ and $y_{33}$, $z_{33}$ are modified (box 86, FIG. 10) by combination with the calibration data to produce two sets of coordinates $y_{cor\ n}$, $z_{cor\ n}$ and $y_{cor\ s}$, $z_{cor\ s}$ corrected for electronic distortion or vignetting, and these latter two sets of values are respectively further modified by the calibration-established factors $W_{32}$ and $W_{33}$ (box 88, FIG. 10) to determine two sets of two-dimensional coordinates $y_{mn}$, $z_{mn}$ and $y_{ms}$, $z_{ms}$. The values $y_{mn}$, $z_{mn}$ are the coordinates of the imaged body portion (corresponding to spot 46n) as projected by X radiation from source 24 on the notional plane $N_n$ perpendicular to axis $x_n$ at the input face of fluoroscope 26. The values $y_{ms}$, $z_{ms}$ are, similarly, the coordinates of the imaged body portion (corresponding to spot 46s) as projected by X radiation from source 25 on the notional plane $N_s$ perpendicular to axis $x_s$ at the input face of fluoroscope 27. With the apparatus of FIG. 2, determination of the sets of coordinates $y_{mn}$, $z_{mn}$ and $y_{ms}$, $z_{ms}$ from the measured sets of image coordinates $y_{32}$, $z_{32}$ and $y_{33}$, $z_{33}$, respectively, is performed by the microcomputer 78.

The next step of the method of the invention is the derivation (box 90, FIG. 10), from the two sets of coordinates $y_{mn}$, $z_{mn}$ and $y_{ms}$, of two sets of three-dimensional spatial coordinates for the imaged body portion, respectively in the two flouroscope coordinate systems $x_n$, $y_n$, $z_{n,s}$ and $x_s$, $y_s$, $z_{n,s}$. Performance of this step incorporates a correction for parallax magnification and, to this end, the step includes a measurement (box 92, FIG. 10) of the positions of the two fluoroscopes 26 and 27 along their respective viewing axes $x_n$ and $x_s$. The position measurements are performed by sensors 70 and 74 in the apparatus of FIG. 2, and transmitted to the microcomputer 78 by digitizers 72 and 76 as digital outputs respectively representing the measured distances $R_n$ and $R_s$ of the input faces of the two fluoroscopes from their positions of maximum extension ($R_{max}$) along their viewing axes.

Figure 8:
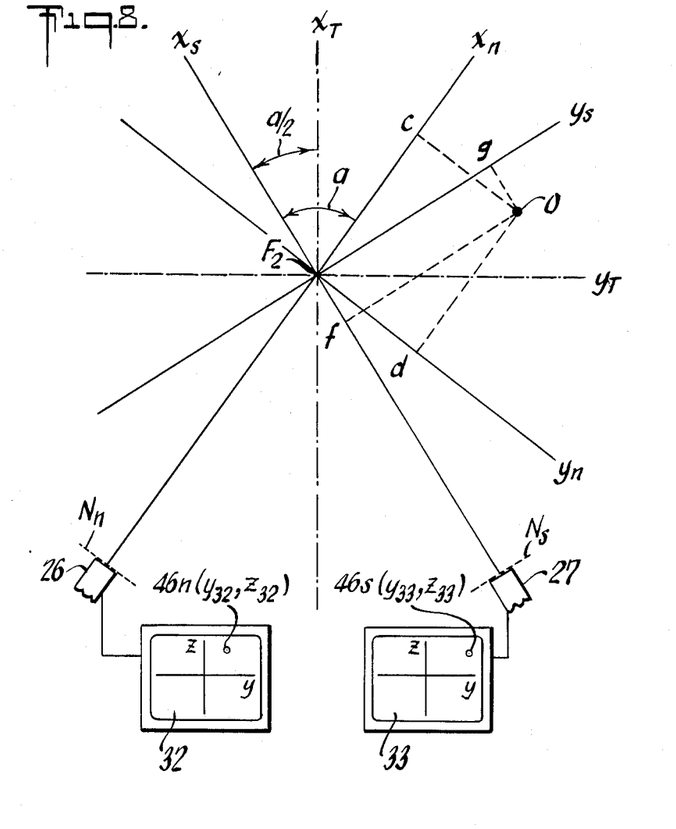
FIG. 8 is a diagram, in the viewing plane, showing the position of an exemplary point relative to the x and y coordinate axes of both fluoroscopes of the FIG. 1 apparatus, and also illustrating the display of that point on the fluoroscope monitors.

The manner in which the two sets of three-dimensional spatial coordinates are derived may be understood from FIG. 8, which is a diagram of the x and y axes of both fluoroscope coordinate systems in the viewing plane, reference also being made to FIG. 7. Assuming that spot O in the viewing plane is the geometric projection thereon of the object or body portion imaged at 46n and 46s on the two screens, the x, y, and z spatial coordinates of this spot are c, d, and e, respectively, in the $x_n$, $y_n$, $z_{n,s}$ coordinate system of fluoroscope 26, and are f, g, and h, respectively, in the $x_s$, $y_s$, $z_{n,s}$ coordinate system of fluoroscope 27. Coordinates c, d, f, and g are represented in FIG. 8.

From the foregoing discussion of FIG. 7, and from the geometrical relationship shown in FIG. 8, it will be apparent that the two sets of coordinates to be derived (c, d, e and f, g, h) are defined by simultaneous equations, which may (for example) be written as $$\frac{y_{mn}}{x_{ppn} + R_n} = \frac{d}{D_{in} + c} \quad (6)$$

$$\frac{y_{ms}}{x_{pps} + R_s} = \frac{g}{D_{ls} + f} \quad (7)$$

$$c = \frac{d\cos(a) - g}{\sin(a)} \quad (8)$$

$$f = \frac{-g\cos(a) + d}{\sin(a)} \quad (9)$$

$$\frac{z_{mn}}{x_{ppn} + R_n} = \frac{e}{D_{in} + c} \quad (10)$$

$$\frac{z_{ms}}{x_{pps} + R_s} = \frac{h}{D_{ls} + f} \quad (11)$$

Equations (6) and (7) are based on the x-y relationship shown in FIG. 7 of the coordinate system of fluoroscope 26, and on the corresponding relationship for the coordinate system of fluoroscope 27. Equations (8) and (9) are based on the showing of FIG. 8. Equations (10) and (11) are based on the x-z relationship of the two fluoroscope coordinate systems respectively corresponding to the x-y relationships exemplified by FIG. 7.

Since $y_{mn}$, $z_{mn}$, $y_{ms}$, $z_{ms}$, $R_n$, $R_s$, $x_{ppn}$, $x_{pps}$, $D_{1n}$, $D_{1s}$, and a are all known either from the above-described calibration procedures or from the preceding steps of the method, the simultaneous equations (6)–(11) can be solved immediately to obtain the two sets of three-dimensional coordinates a, d, e and f, g, h, in the respective coordinate systems $x_n$, $y_n$, $z_{n,s}$ and $x_s$, $y_s$, $z_{n,s}$. With the apparatus of FIG. 2, this solution of the equations is performed by the microcomputer 78. It will be understood that, both in determining $y_{mn}$, $z_{mn}$ and $y_{ms}$, $z_{ms}$ from $y_{32}$, $z_{32}$ and $y_{33}$, $z_{33}$, and in deriving c, d, e and f, g, h by setting up and solving equations (6)–(11), consistent sign conventions must be maintained; conveniently, these sign conventions are chosen so as to agree with the sign convention of the machine coordinate system $x_o$, $y_o$, $z_o$ as established in the control instrumentalities of the ESWL apparatus 10.

Further in accordance with the method of the invention, the derived sets of coordinates c, d, e and f, g, h are transformed into a single set of three-dimensional coordinates of the imaged body portion in a common coordinate system, viz. the machine coordinate system. To accomplish this transformation, the two fluoroscope coordinate systems are first rotated about their common $Z_{n,s}$ axis with an equal but opposite angular displacement a/2 in the viewing plane (box 94, FIG. 10) until their respective y axes ($y_n$ and $y_s$) coincide in a common y axis, $y_t$; their respective x axes then also coincide in the common x axis, $x_t$. In this new, common coordinate system, the x and y axes $x_t$ and $y_t$ both still lie in the viewing plane; the z axis is still $z_{n,s}$; $x_t$ and $z_{n,s}$ both lie in the $x_o$-$z_o$ plane; and the axis $y_t$ coincides with the axis $y_o$ of the machine coordinate system (compare FIGS. 3 and 8). As will be appreciated, "rotation" of one coordinate system into another is the operation of mathematically deriving, from the spatial coordinates of a point in one coordinate system, the spatial coordinates of the same point in the second system, given the angular displacement between the two coordinate systems. This operation is again performed, in the FIG. 2 apparatus, by the microcomputer 78.

The common coordinate system $x_t$, $y_t$, $z_{n,s}$ thus established is rotated (box 96, FIG. 10) about its axis $y_t$ (coincident with axis $y_o$) until it coincides with the machine coordinate system; i.e., it is rotated through the angle r (FIG. 3), which is the angle between the viewing plane and the horizontal $x_o$-$y_o$ plane. Once more, the transformation is performed, in the FIG. 2 apparatus, by the microcomputer.

Figure 9:
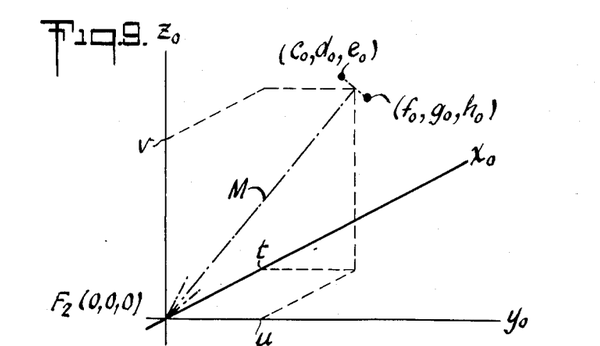
FIG. 9 is a diagram of the coordinate system of FIG. 3 in explanation of further features of the aforementioned embodiment of the present method.

Theoretically, if spots 46n and 46s are images of the same object or body portion, the machine coordinate system transforms $c_o$, $d_o$, $e_o$ of coordinates c, d, e in the coordinate system of fluoroscope 26 should coincide with the machine coordinate system transforms $f_o$, $g_o$, $h_o$ of coordinates f, g, h in the coordinate system of fluoroscope 27. In practice, however, this coincidence ordinarily does not occur, owing to imprecision in measuring or modifying the initial screen coordinates $y_{32}$, $z_{32}$ and $y_{33}$, $Z_{33}$. Thus, when the transformation of coordinates c, d, e and f, g, h into the common machine coordinate system $x_o$, $y_o$, $z_o$ has been accomplished, there usually are two sets of transformed coordinates $c_o$, $d_o$, $e_o$ and $f_o$, $g_o$, $h_o$ respectively identifying two locations spaced apart from each other, as shown in FIG. 9. In such case, as a further feature of the invention, the distance between points $c_o$, $d_o$, $e_o$ and $f_o$, $g_o$, $h_o$ is determined and compared with a predetermined value, e.g. a value of 1 cm. If the distance between the points is less than or equal to the predetermined value, then $c_o$, $d_o$, $e_o$ and $f_o$, $g_o$, $h_o$ are assumed to represent the same object or body portion, and the coordinates t, u, v (in the machine coordinate system) of the midpoint between them are derived and are taken as the coordinates of the body portion to be positioned (box 98, FIG. 10). If the distance between the two points exceeds the predetermind value, then the identity of the objects imaged at 46n and 46s is doubtful, and it is necessary to repeat the viewing of the patient through the fluoroscope (and the subsequent steps of the method) in order to locate and derive data from images of the same body portion on the two screens; but with an operator having ordinary skill in the examination of fluoroscope images, this will be a relatively infrequent occurrence.

From the three midpoint coordinates t, u, v thus established (or from the three coordinates $c_o = f_o$, $d_o = g_o$, and $e_o = h_o$, if the two sets of coordinates $c_o$, $d_o$, $e_o$ and $f_o$, $g_o$, $h_o$ happen to coincide), there is directly ascertained a displacement vector $\vec{M}$ (box 100, FIG. 10) representing the magnitude and direction of motion of the body P necessary to bring the imaged body portion to $F_2$. With the same sign conventions as before still maintained, this information is added to the gantry coordinates currently shown in XYZ display 18 to determined the gantry coordinates for which the body portion will be at $F_2$ (box 102, FIG. 10), and the gantry is moved until it reaches the position represented by the last-mentioned coordinates. Such motion may be rectilinear or (if necessary to avoid possibly damaging contact of the cradle with the focusing chamber) it may be circuitous; in either event, the resultant motion of the gantry has the magnitude and direction of vector M.

The operations of determining the distance between $c_o$, $d_o$, $e_o$ and $f_o$, $g_o$, $h_o$; comparing that distance with a predeterined value; upon finding that the compared distance is less than the predetermined value, calculating the coordinates t, u, v of the midpoint between $c_o$, $d_o$, $e_o$ and $f_o$, $g_o$, $h_o$; and deriving therefrom the magnitude and direction of motion represented by vector M, may all be performed by the microcomputer, to provide a digital readout for use by the operator in moving the gantry. Alternatively, the microcomputer may interface directly with the gantry controls to effect the requisite positioning motion. In any event, the patient is exposed to X-rays only for a time sufficient to produce the initial images on screens 32 and 33 from which the values $y_{32}$, $z_{32}$, and $y_{33}$, $z_{33}$ are determined; no repetition or continuation of irradiation during movement of the patient is required.

Although the method of the invention has been described as used to position a small internal body portion at $F_2$, it could also be employed, for instance, to position the body portion at some other predetermined location if desired.

It is to be understood that the invention is not limited to the procedures and embodiments herein specifically set forth, but may be carried out in other ways without departure from its spirit.

I claim:

1. A method of positioning a small internal portion of a body at a predetermined point relative to an extracorporeal referent, said body portion being detectable by penetrating radiation and said body being initially so disposed that the body portion is generally adjacent said predetermined point, said method comprising
    (a) viewing said body with penetrating radiation along two convergent viewing axes intersecting at said predetermined point for producing two images of the interior of the body as viewed by said penetrating radiation respectively along said two viewing axes, each of said images including a portion representing said body portion;
    (b) determining, from said two images, two-dimensional coordinates of the projections of the imaged body portion by the pentrating radiation on two notional planes respectively perpendicular to the viewing axes of the images, thereby to establish two sets of two-dimensional body portion coordinates, one for each image;
    (c) from said two sets of two-dimensional coordinates, deriving for each image spatial coordinates of the imaged body portion in a coordinate system having as one axis the viewing axis of the image, thereby to establish two sets of three-dimensional body portion coordinates, one for each image;
    (d) transforming said two sets of three-dimensional coordinates into a single set of three-dimensional coordinates in a common coordinate system in which the coordinates of said predetermined point are known, said single set of three-dimensional coordinates representing the location of said body portion in said last-mentioned system, thereby to determine the magnitude and direction of movement of said body required to position said body portion at said predetermined point; and
    (e) displacing said body with a resultant motion having said magnitude and direction.

2. A method according to claim 1, wherein the viewing step is performed by directing penetrating radiation, from two sources of radiation disposed below the body, respectively along each of said two viewing axes through the body; receiving penetrating radiation from said sources, after passage of the radiation through the body, with two radiation detectors disposed above the body and respectively aligned with the two viewing axes, each of said detectors producing an output convertible into a two-dimensional image of the body volume through which radiation received by that detector has passed, in an image plane perpendicular to the viewing axis with which that detector is aligned; and converting the output of each detector into such two-dimensional image.

3. A method according to claim 2, wherein the position of the imaged body portion on each said image relative to a referent representing a coordinate system in the notional plane perpendicular to the viewing axis of that image differs from the position of the body portion projection on the last-mentioned notional plane relative to the last-mentioned coordinate system by ascertainable factors, and wherein the coordinate-determining step comprises
    (i) identifying, on each said image, a portion thereof representing said body portion;
    (ii) measuring the position of the identified image portion on each said image relative to said last-mentioned referent, thereby to obtain apparent two-dimensional coordinates for the identified image portion on each said image;
    (iii) ascertaining said factors for each said image; and
    (iv) modifying the apparent two-dimensional coordinates by the ascertained factors for each said image to establish said two sets of two-dimensional coordinates.

4. A method according to claim 3, wherein the two-dimensional coordinates of the body portion projection on each said notional plane differ, from the spatial coordinates of the body portion geometrically projected in a plane parallel to the notional plane and containing said predetermined point, by a parallax deviation dependant, for each image, on the distance between source and detector along the viewing axis of the image; and wherein the deriving step includes measuring the last-mentioned distance for each image and deriving said two set of three-dimensional coordinates from these measurements and from the two sets of two-dimensional coordinates, preestablished measurements of the disntances between the radiation sources and the predetermined point, and a preestablished measurement of the angle between the two viewing axes.

5. A method according to claim 4; wherein each said image is produced on a cathode ray tube; wherein said factors include vignetting and electronic magnification; wherein the factor-ascertaining step includes ascertaining calibration values, for each image, to compensate for vignetting and electronic magnification; and wherein the modifying step includes applying said calibration values to said apparent coordinates.

6. A method according to claim 5, wherein said two sets of three-dimensional coordinates are established, respectively, with reference to two three-dimensional rectangular coordinate systems each having said predeterined point as origin, an x axis coincident with one of said viewing axes, a y axis coplanar with both said viewing axes, and a z axis coincident with the z axis of the other of said two last-mentioned three-dimensional coordinate systems, said viewing axes lying in a common plane oblique to the horizontal; and wherein the transforming step comprises
    (i) rotating both of the last-mentioned coordinate systems about their coincident z axes until their y axes coincide to constitute a common coordinate system;

(ii) rotating the last-mentioned common coordinate system about the y axis thereof until the x and y axes lie in a horizontal plane, constituting a common coordinate system with a vertical z-axis having therein two sets of three-dimensional coordinates;

(iii) determining the distance between the spatial locations respectively represented by the two sets of three-dimensional coordinates; and (iv) upon ascertaining that said distance is less than a predetermined value, determining the three-dimensional coordinates, in said last-mentioned common coordinate system, of the midpoint between said spatial locations, thereby to establish said single set of three-dimensional coordinates.

7. A method according to claim 1, wherein said two sets of three-dimensional coordinates are established, respectively, with reference to two three-dimensional rectangular coordinate systems each having said predetermined point as origin, an x axis coincident with one of said viewing axes, a y axis coplanar with both said viewing axes, and a z axis coincident with the z axis of the other of said two last-mentioned three-dimensional coordinate systems; and wherein the transforming step comprises rotating both of the last-mentioned coordinate systems about their coincident z axes until their y axes coincide to constitute a common coordinate system.

8. A method according to claim 7, wherein the two viewing axes lie in a common plane oblique to the horizontal, and wherein the transforming step further includes rotating the last-mentioned common coordinate system about the y axis thereof until the x and y axes lie in a horizontal plane.

9. A method according to claim 1, wherein the transforming step comprises
   (i) transforming said two sets of three-dimensional coordinates into a common coordinate system to provide therein two sets of three-dimensional coordinates;
   (ii) determining the distance between the spatial locations respectively represented by the two seets of three-dimensional coordinates;
   (iii) upon ascertaining that said distance is less than a predetermined value, determining the three-dimensional coordinates, in said last-mentioned common coordinate system, of the midpoint between said spatial locations, thereby to establish said single set of three-dimensional coordinates.

* * * * *